US009814386B2

(12) United States Patent
Abramoff et al.

(10) Patent No.: US 9,814,386 B2
(45) Date of Patent: Nov. 14, 2017

(54) SYSTEMS AND METHODS FOR ALIGNMENT OF THE EYE FOR OCULAR IMAGING

(71) Applicant: IDx, LLC, Iowa City, IA (US)

(72) Inventors: Michael Abramoff, University Heights, IA (US); Eric Talmage, Byron Center, MI (US); Ben Clark, Iowa City, IA (US); Edward DeHoog, Long Beach, CA (US); Timothy Chung, Iowa City, IA (US)

(73) Assignee: IDx, LLC, Iowa City, IA (US)

( * ) Notice: Subject to any disclaimer, the term of this patent is extended or adjusted under 35 U.S.C. 154(b) by 129 days.

(21) Appl. No.: 14/791,028

(22) Filed: Jul. 2, 2015

(65) Prior Publication Data
US 2016/0183788 A1    Jun. 30, 2016

Related U.S. Application Data

(60) Provisional application No. 62/020,252, filed on Jul. 2, 2014.

(51) Int. Cl.
*A61B 3/14* (2006.01)
*A61B 3/15* (2006.01)
*A61B 3/00* (2006.01)
*A61B 3/12* (2006.01)

(52) U.S. Cl.
CPC ............ *A61B 3/152* (2013.01); *A61B 3/0008* (2013.01); *A61B 3/12* (2013.01)

(58) Field of Classification Search
CPC .. A61B 3/15; A61B 3/152; A61B 3/12; A61B 3/0008
USPC ................................ 351/205, 206, 208, 246
See application file for complete search history.

(56) References Cited

U.S. PATENT DOCUMENTS

| | | | |
|---|---|---|---|
| 5,442,412 A | 8/1995 | Frey et al. |
| 6,361,495 B1 | 3/2002 | Grolman |
| 6,490,365 B2 | 12/2002 | Horiguchi et al. |
| 6,554,428 B2 | 4/2003 | Fergason et al. |
| 6,873,714 B2 | 3/2005 | Witt et al. |
| 7,210,782 B2 | 5/2007 | Imaoka et al. |
| 7,416,305 B2 | 8/2008 | Williams et al. |
| 7,620,147 B2 | 11/2009 | Gertner et al. |
| 8,388,134 B2 | 3/2013 | Goldstein et al. |
| 8,444,268 B2 | 5/2013 | Hammer et al. |

(Continued)

FOREIGN PATENT DOCUMENTS

WO    2012176026    12/2012

OTHER PUBLICATIONS

Heidelberg Engineering, Inc, "http://www.heidelbergengineering.com/us/technology/", Dec. 31, 2008.

(Continued)

*Primary Examiner* — James Greece
(74) *Attorney, Agent, or Firm* — Davis, Brown, Koehn, Shors & Roberts, P.C.; Matthew W. Coryell

(57) ABSTRACT

An ocular alignment system for aligning a subject's eye with an optical axis of an ocular imaging device comprising one or more guide light and one or more baffle configured to mask the one or more guide light from view of the subject such that the one or more guide light is only visible to the subject when the eye of the subject is aligned with the optical axis of an ocular imaging system.

19 Claims, 16 Drawing Sheets

(56) References Cited

U.S. PATENT DOCUMENTS

| | | |
|---|---|---|
| 8,449,112 B2 | 5/2013 | Kishida |
| 8,596,788 B2 | 12/2013 | Ranchod |
| 2003/0067680 A1 | 4/2003 | Weinstein et al. |
| 2006/0077344 A1 | 4/2006 | Kashiwagi et al. |
| 2006/0271027 A1* | 11/2006 | Silvestrini et al. ............... 606/4 |
| 2010/0310133 A1 | 12/2010 | Mason et al. |
| 2011/0234978 A1 | 9/2011 | Hammer et al. |
| 2011/0237999 A1 | 9/2011 | Muller et al. |
| 2013/0033593 A1 | 2/2013 | Chinnock et al. |
| 2013/0250243 A1 | 9/2013 | Cech |
| 2013/0278898 A1 | 10/2013 | Kato |
| 2013/0301002 A1 | 11/2013 | Gruppetta |

OTHER PUBLICATIONS

Sharp et al., "Laser Imaging of the Retina", Dec. 31, 1999, Publisher: Br F Ophthalmol.

\* cited by examiner

SYSTEMS AND METHODS FOR ALIGNMENT OF THE EYE FOR OCULAR IMAGING

CROSS-REFERENCE TO RELATED APPLICATION(S)

This application claims the benefit of priority of U.S. Provisional Patent Application Ser. No. 62/020,252 filed on Jul. 2, 2014, which is incorporated herein by reference for all purposes.

FIELD OF THE INVENTION

Disclosed herein are systems and methods for alignment of the eye for ocular imaging.

BACKGROUND OF THE INVENTION

In ocular imaging, proper alignment of the optical axes of the subject's eye and the imaging optics is a prerequisite to avoid unwanted reflections quality ocular image acquisition. However, there are 12 degrees of freedom (6 on the part of the subject's eye, and 6 on the part of the imaging system, making this a nontrivial task. Traditional approaches to achieving alignment rely on an operator manually aligning the axes of the imaging device to that of the subject's eye, or robotic (automated) alignment of the axes of the imaging system to that of the subject's eye. Both trained operators and robotic alignment add cost and complexity to the imaging workflow. For example, manual handheld fundus cameras require the operator to manually position a camera in three-dimensional space along 6 degrees of freedom, and often require an integrated screen to view the eye, while the head of the subject is partially restrained leaving 3 degrees of freedom, for a total of 9 degrees of freedom. Traditional manual desk-mounted fundus cameras require the operator to manually steer the camera with a joystick, 6 degrees of freedom, while the subject's eye is restrained with a chinrest and headband as well as fixation, leaving 6 degrees of freedom in total. Automated or semi-automated fundus cameras require complex motors, additional cameras and sensors, and built-in image processing to drive the automated alignment along 6 degrees of freedom, thereby adding significant cost, and also restrain the subject's eye using chinrest, headband and fixation.

The human eye, however, is the endpoint for a highly versatile cybernetic system that can align the optical axis of the eye with respect to external objects along 6 degrees of freedom. Because there is a need in the art for an alignment system with reduced cost, complexity, and ease of operation, it is attractive to use the natural alignment of the human body.

BRIEF SUMMARY OF THE INVENTION

Disclosed herein are various ocular alignment system embodiments for aligning a subject's eye with an optical axes of an ocular imaging device. The implementations comprise one or more guide lights and one or more baffles configured to mask the one or more guide lights from the subject's eye such that the one or more guide light is only visible to the subject when the optical axis eye of the subject is aligned with the optical axis of an ocular imaging system along one or more degrees of freedom.

In certain aspects, disclosed is a device for aligning the optical axis of a subject's eye with the optical axis of an ocular imaging device comprising a housing, the housing comprising a first end, a second end, an outer surface, and an inner surface, wherein the inner surface defines a luminal space and wherein the luminal space is configured to allow for passage of the optical axis therethrough; a plurality of guide light assemblies disposed within the housing, each guide light assembly comprising a body, the body comprising a first side and a second side opposite the first side, wherein the second side faces the luminal space a channel defined in the body, wherein the channel extends from the body first side to the body second side, wherein the channel forms an opening in the body second side; a guide light disposed within the channel, wherein the guide light is configured to emit rays out of the opening; and a baffle disposed transversely in the channel between the guide light and the opening and configured to mask rays from the guide light, wherein the baffle further comprises a slit configured to allow passage of rays along a path of ocular alignment; and a plurality of secondary baffle assemblies disposed on the housing second end, wherein each of the plurality of second baffle assemblies is configured to mask rays emitted from one of the plurality of guide light assemblies, wherein each of secondary baffle assemblies further comprises a slit configured to allow passage of rays along a second path of ocular alignment, wherein the rays from each of the plurality of guide light assemblies are visible to the subject when the optical axis of the subject's eye is in alignment with respect to the optical axis of the device and not visible when the optical axis of the subject's eye is out of alignment with respect to the optical axis of the device.

In further aspects, disclosed is a method of aligning the optical axis of a subject's eye with the optical axis of an ocular imaging device comprising providing a first set of guide lights along the line connecting the optical axes of the subject's eye and of the ocular imaging device; and providing one or more baffles, configured to mask the rays emitted from first set of guide lights from view of the subject such that first set of guide lights is only visible to the subject when the eye of the subject is aligned with the optical axis of an ocular imaging system.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The instant disclosure relates to optical imaging system embodiments for imaging the eye of a subject which allow a subject to properly position and align the optical axis of his eye with the optical axis of an ocular imaging system in response to visual cues from the system. This is in contrast to known optical imaging systems where the subject's eye position is fixated as much as possible and alignment is achieved by adjusting the position of camera elements with respect to that eye. Thus, the disclosed implementations utilize the precise oculomotor alignment system of the human eye to align to the optical axis of the imaging system, instead of relying on the trained operators or expensive servo motors to align the optical axis of the imaging system to that of the human eye. The disclosed systems are further able to provide for precise oculomotor alignment without the use of mirrors or lenses to direct light to the desired angle along the optical path.

According to certain embodiments, the system comprises a camera (for example a fundus camera) having an image sensor and one or more guide lights positioned laterally between the image sensor and the subject's eye. In certain embodiments, the system further comprises one or more baffles positioned between the one or more guide light and subject's eye. The one or more baffle is configured to occlude the subject's view of the one or more guide light until the eye of the subject is properly positioned and aligned translationally (along x, y, z axes). Further embodiments have additional lights to provide for alignment rotationally (along θ, η, and ζ axes) with respect to the optical path of the imaging device, resulting in optimal image acquisition.

Figure 1A:
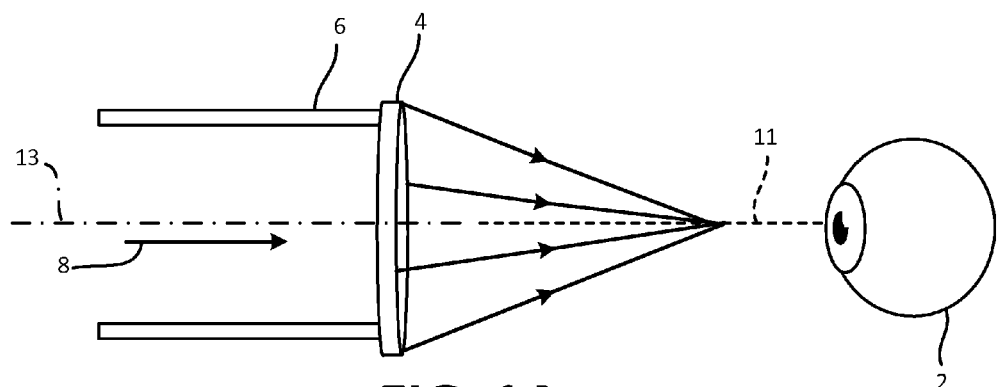
FIGS. 1A and 1B are schematic diagrams of the system, according to certain embodiments.
Figure 1B:
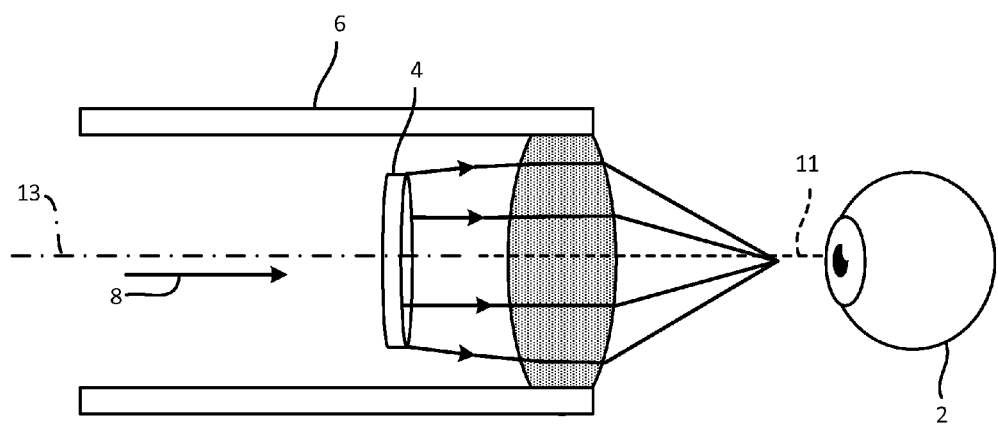
Figure 2A:
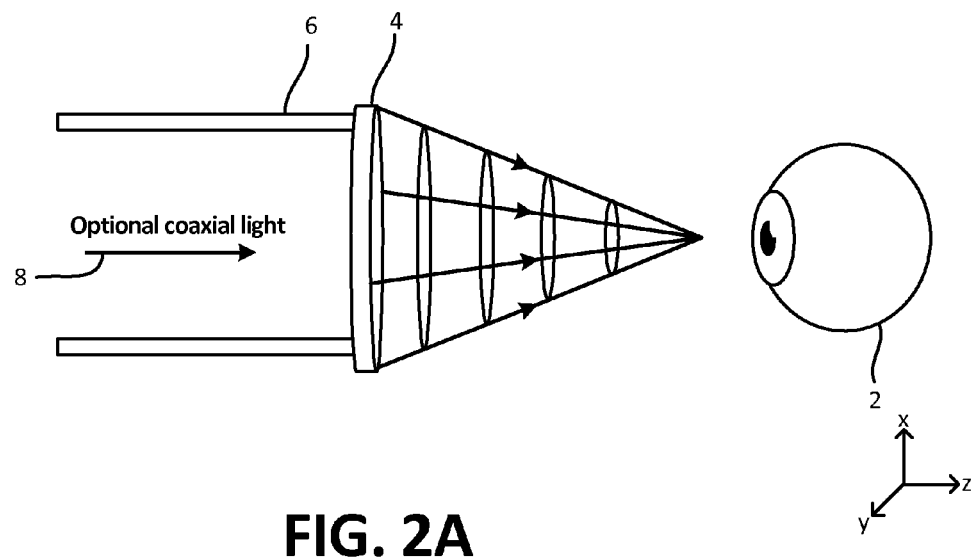
FIGS. 2A and 2B are schematic diagrams of the system, according to certain embodiments.

In certain embodiments, as best seen in FIGS. 1 and 2, the guide light is a ring light 4, which is a light forming a substantially ring-like shape. As best shown in FIG. 2A, the guide light 4 is masked by a baffle 10, which, according to certain embodiments, is of a substantially cone-like shape with the wide end 12 of the cone-like shaped baffle 10 at the ring guide light 4 and the narrow end 14 near the eye of the subject 2. In certain embodiments, as the subject approaches the device, a coaxial light 8 becomes visible to aid in coarse alignment of the subject's eye 2 with the system. As the subject directs its gaze into the device, some section of the guide light ring 4 comes into view. As the subject further adjusts its gaze toward alignment, more and more of the ring 4 becomes visible until the entire ring 4 is visible indicating that the subject's optical axis 11 is in alignment with the to the optical axis of the imaging system 13 has been achieved. During this process, the aspect of the ring 4 that is not visible will direct the subject to adjust its eye 2 in the appropriate direction for alignment. For example, if the right side of the ring 4 is fully visible but the left is not, then the subject adjusts its eye 2 to the right until the light becomes visible.

According to certain embodiments, best shown in FIG. 1A, the system is external to the ocular imaging device 6 (also referred to as a "camera"). For example, in certain embodiments, the guide lights 4 are positioned on a ring 4 between the objective lens of the camera 6 and the subject's eye 2. According to certain alternative embodiments, best shown in FIG. 1B, the system is integrated into the ocular imaging device 6. In certain embodiments, the guide lights 4 are positioned around the objective lens of the camera 6. In further embodiments, the guide lights 4 are positioned within the optics of a fundus camera, or other optical device, in the illumination pathway. In certain embodiments, the guide lights are discretely arranged around the optical opening of an optical imaging device.

Figure 2B:
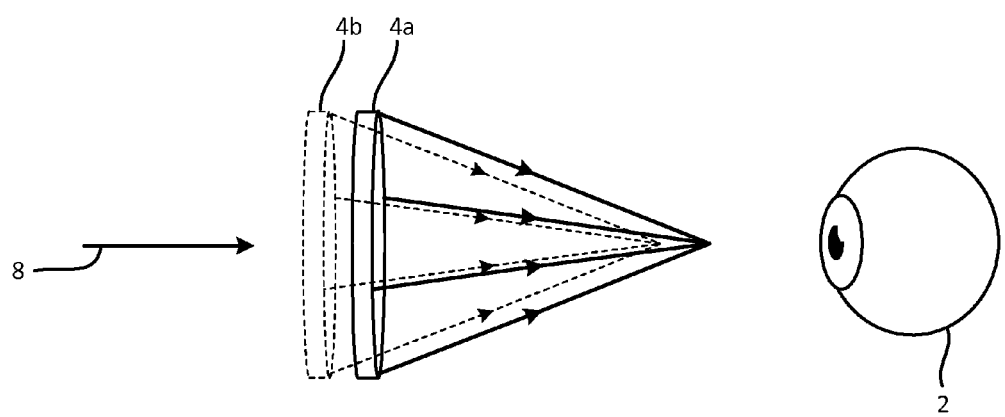

According to certain embodiments, best shown in FIG. 2B, additional direction is provided to the subject by providing a sequence of lights that serve as sequential focal points. By way of example, a first guide light or set of guide lights 4a is activated and the subject aligns its eye 2 with the system such that the guide light 4 or each of the set of guide lights 4 is visible. Next, a second guide light or set of guide lights 4b is activated at a point further down the optical path (more distal from the eye 2 of the subject). The second set of guide lights 4b requires a more precise level of alignment in order to become visible to the subject, relative to the first guide light or set of guide lights 4a. In certain embodiments, additional subsequent guide lights are presented to the subject with increasing levels of precision required of the alignment in order for the lights to become visible. As the subject aligns its eye 2 with each of the sequential focal points, the subject's eye 2 is guided along the z-axis until they are looking at the target ring of light.

In certain embodiments, one or more of the guide lights 4 are implemented as collimated light sources such as laser light. In these embodiments, the one or more guide lights 4 can be direct along a specific path configured to be visible only when the eye 2 is properly positioned. Accordingly, in these implementations, baffles are no longer necessarily needed.

Figure 3A:
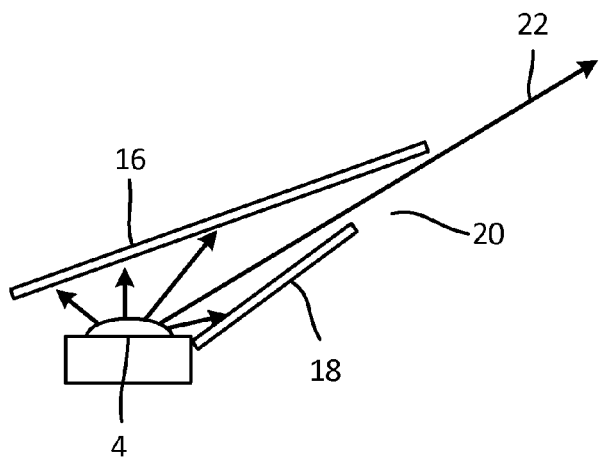
FIGS. 3A and 3B show schematic diagrams of is a schematic diagram of guide lights and baffles according to certain embodiments.
Figure 3B:
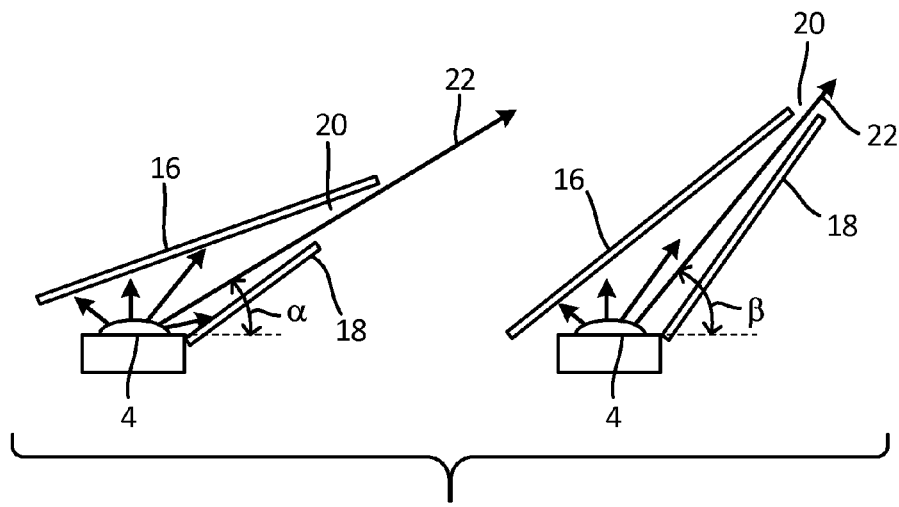

FIGS. 3A and B show exemplary baffles 16, 18 according to certain embodiments. In these embodiments, light emitted from the guide light 4 is constrained by a first baffle 16 and a second baffle 18. The first baffle 16 and second baffle 18 define a gap 20 through which a guide light beam 22 along the alignment path is emitted. As will be appreciated by one skilled in the art, the angle of the baffle(s) 16, 18 constrains the light emission such that only a beam 22 at the desired beam path angle is emitted, allowing for precise control of the position of the eye required for viewing the masked light. As best shown in FIG. 3B, baffle angle can be adjusted to produce emission of the alignment beam 22 at the desired angle.

In certain alternative embodiments, the one or more guide lights are further comprised of sets of guide lights, wherein each set is configured to achieve alignment with respect to a specific axis (not shown). For example, according to certain embodiments, the plurality of guide lights are further comprised of one or more of z-axis guide lights, configured to be visible when the subject's eye is optimally positioned along the z-axis with respect to the image sensor. The plurality of guide lights are further comprised of one or more x-axis guide lights and one or more y-axis guide lights, configured to be visible to the subject when the subject is optimally positioned and aligned along the x-axis and y-axis, respectively.

Figure 4A:
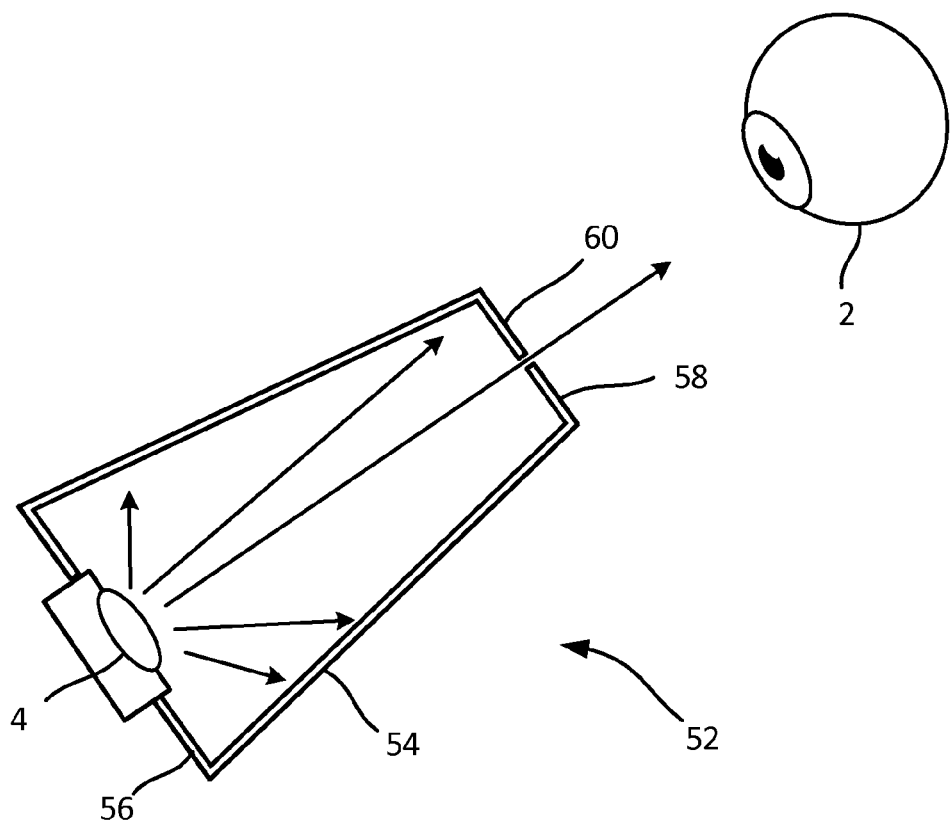
FIGS. 4A and 4B are a schematic diagrams of a baffle chambers, according to certain embodiments.
Figure 4B:
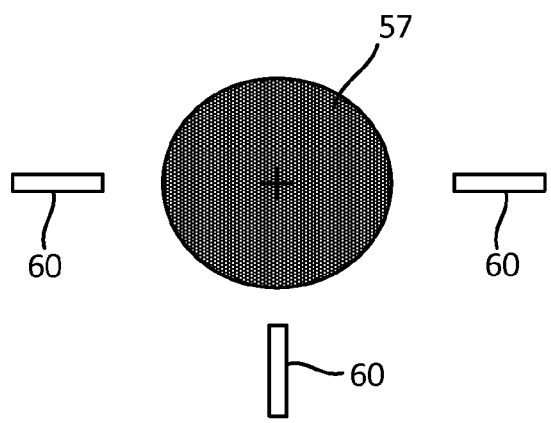
Figure 13:
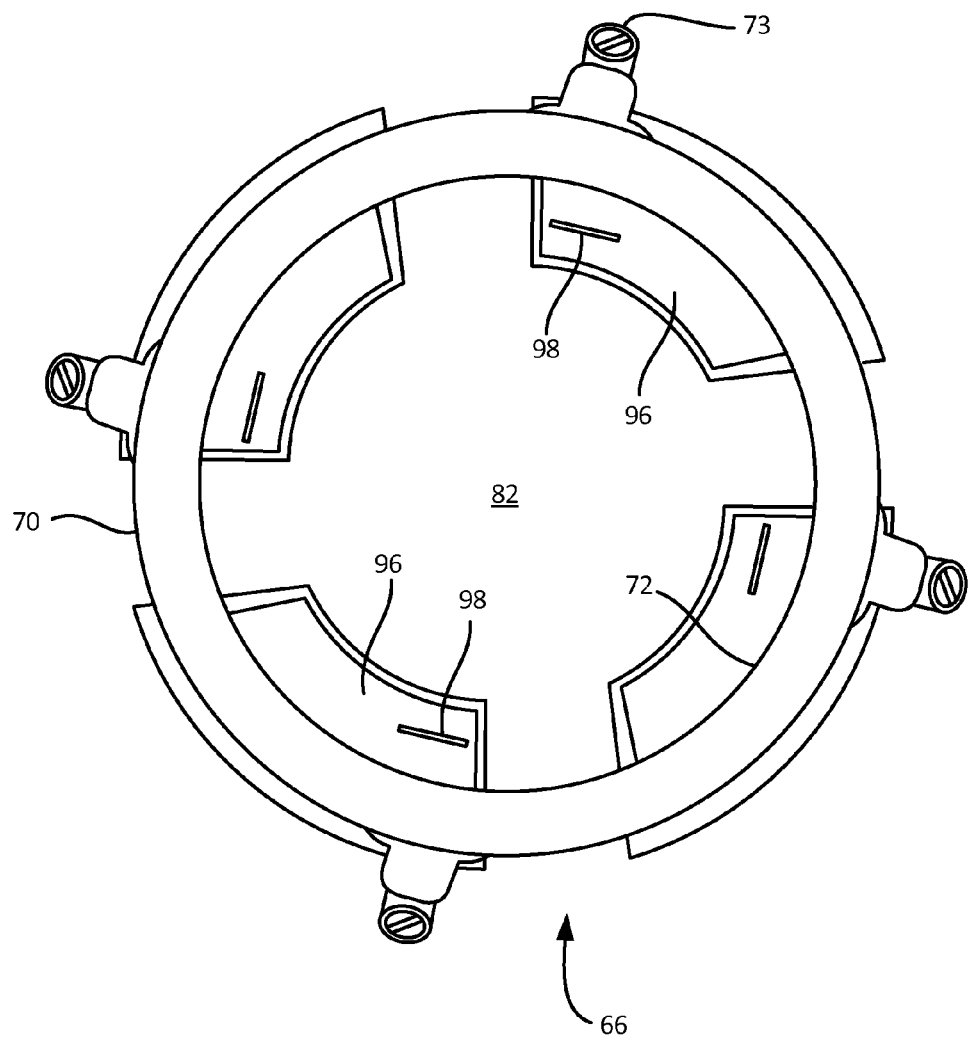
FIG. 13 is a bottom view of the ocular alignment device, according to certain embodiments.

According to certain implementations, best shown in FIG. 4A, each of the one or more guide lights 4, is enclosed within a baffle chamber 52. The baffle chamber 52 is defined by baffle walls 54 and has a first end 56, at which the guide light is positioned, and a second end 58, from which the light is emitted. In certain embodiments, the baffle chamber 52 narrows from the first end 56 to the second end 58, and in certain embodiments, forms a substantially cone-like shape. In certain implementations, light is emitted from the second end 58 through a baffle chamber slit 60. The baffle chamber slit 60 ensures that only light that leaves the baffle chamber 52 is traveling at the proper angle to achieve alignment with the subjects eye (not shown). According to certain embodiments, the baffle chamber walls 54 are comprised of an anti-reflective material, thus further ensuring that only light at the proper angle leaves the baffle chamber 52. In further embodiments, air pockets or voids within the baffle chamber 52 are employed to further minimize reflection. According to certain embodiments, best shown in FIG. 4B, the According to certain embodiments, best shown in FIG. 13, the baffle slits 60 are angled toward the center of the optical path 57. In certain implementations, the baffle chamber is a guide light assembly, a described elsewhere herein.

Figure 5:
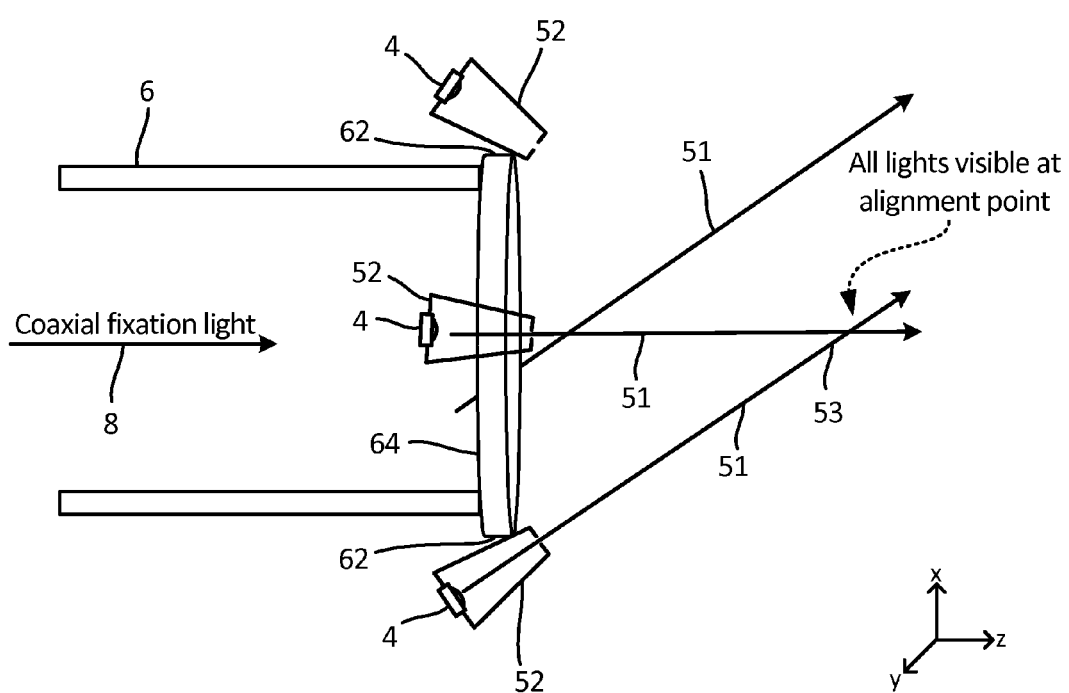
FIG. 5 is a schematic diagram of the system according to certain embodiments.

In certain implementations, best shown in FIG. 5, there are multiple baffle chambers 52. In this specific example, there are three baffle chambers 52. The guide lights 4 are disposed within the baffle chambers 52 and the baffle chambers 52 are mounted on a housing 64 configured to interface with an optical imaging device 6. According to certain embodiments, the baffle chambers 52 are pivotally mounted on the housing 64, such as by way of a hinge 62. In these embodiments, the angle of the baffle chamber 52, and thus the angle of the emitted guide light beam 51, is adjusted according to the desired ocular alignment point 53. According to certain implementations, the pivotal movement of the baffle chambers 52 around their hinges 62 is driven by an electric motor or the like so that the baffle chambers 52 can be pivoted according to predetermined angles corresponding with various desired points of alignment.

Figure 6:
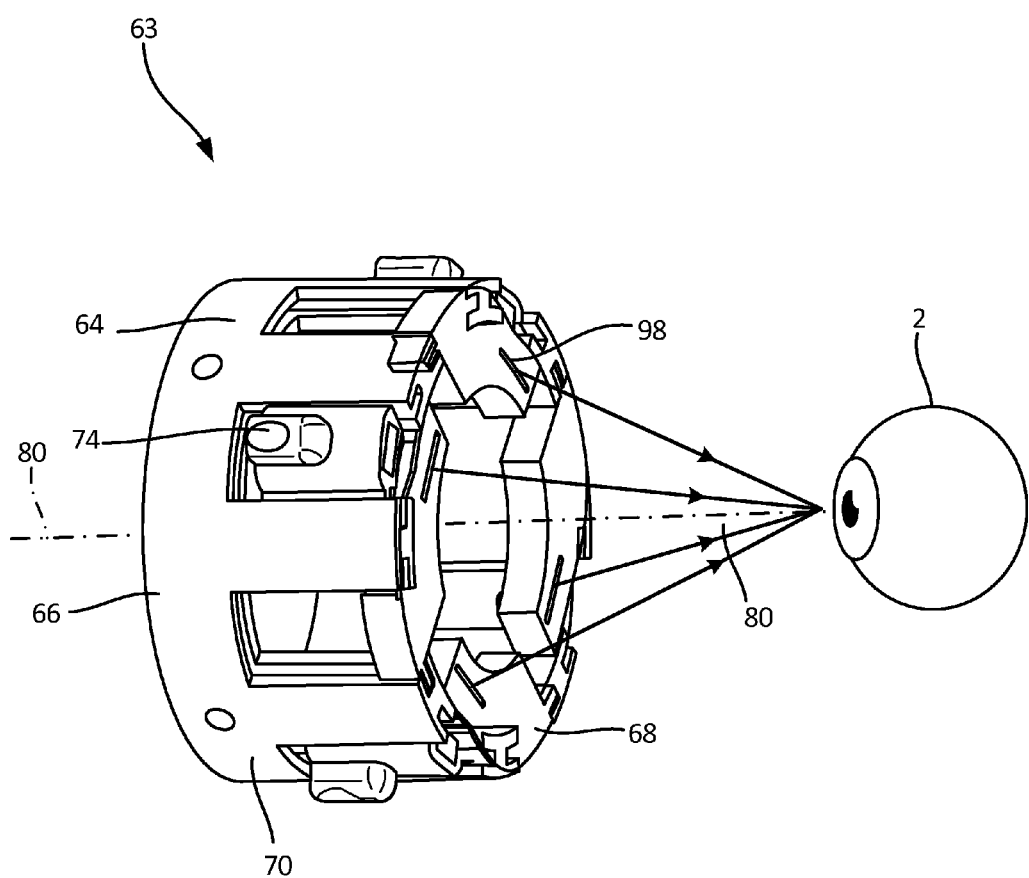
FIG. 6 is a perspective view of the ocular alignment device, according to certain embodiments.
Figure 7:
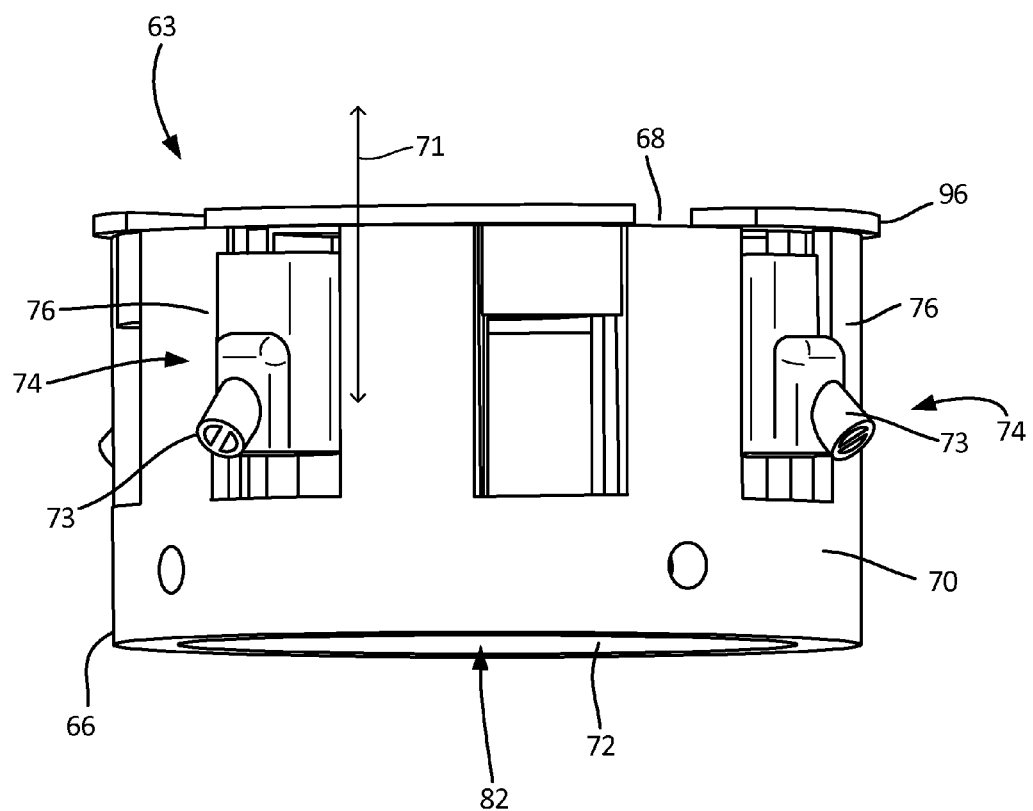
FIG. 7 is a side view of the ocular alignment device, according to certain embodiments.
Figure 11:
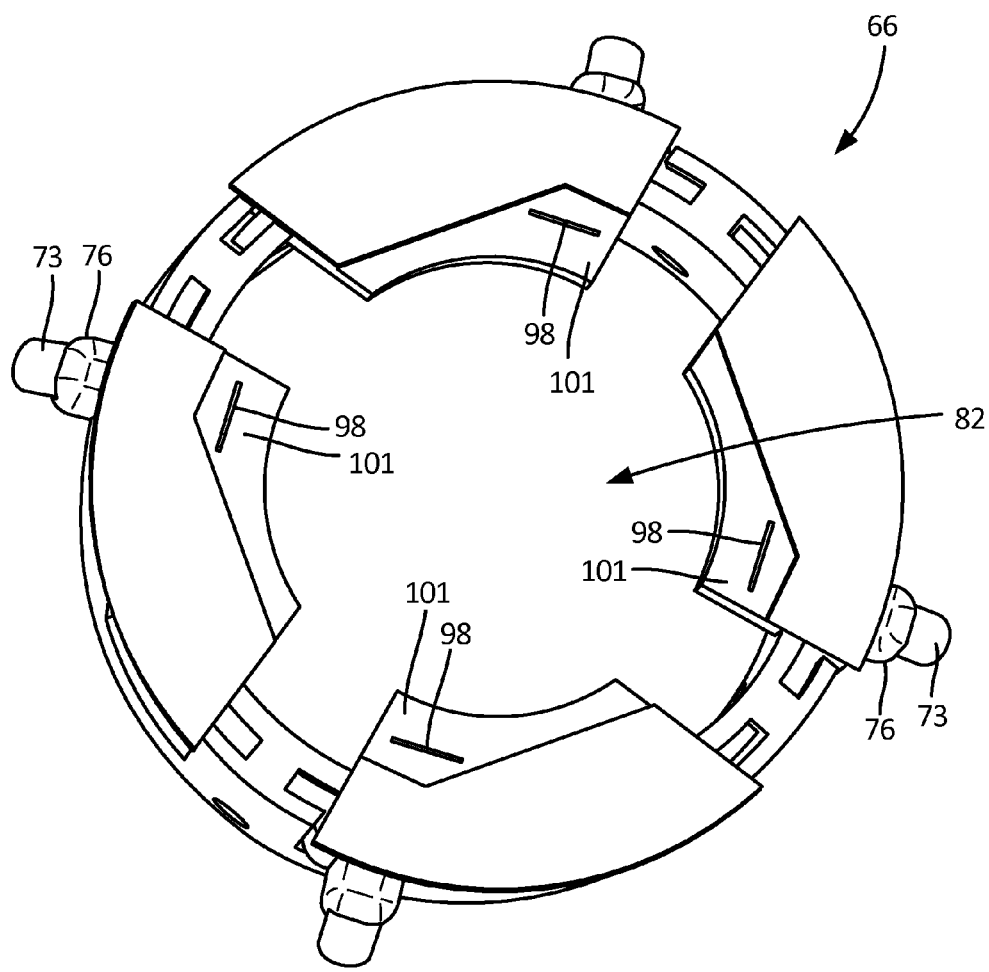
FIG. 11 is a top view of the ocular alignment device, according to certain embodiments.
Figure 12:
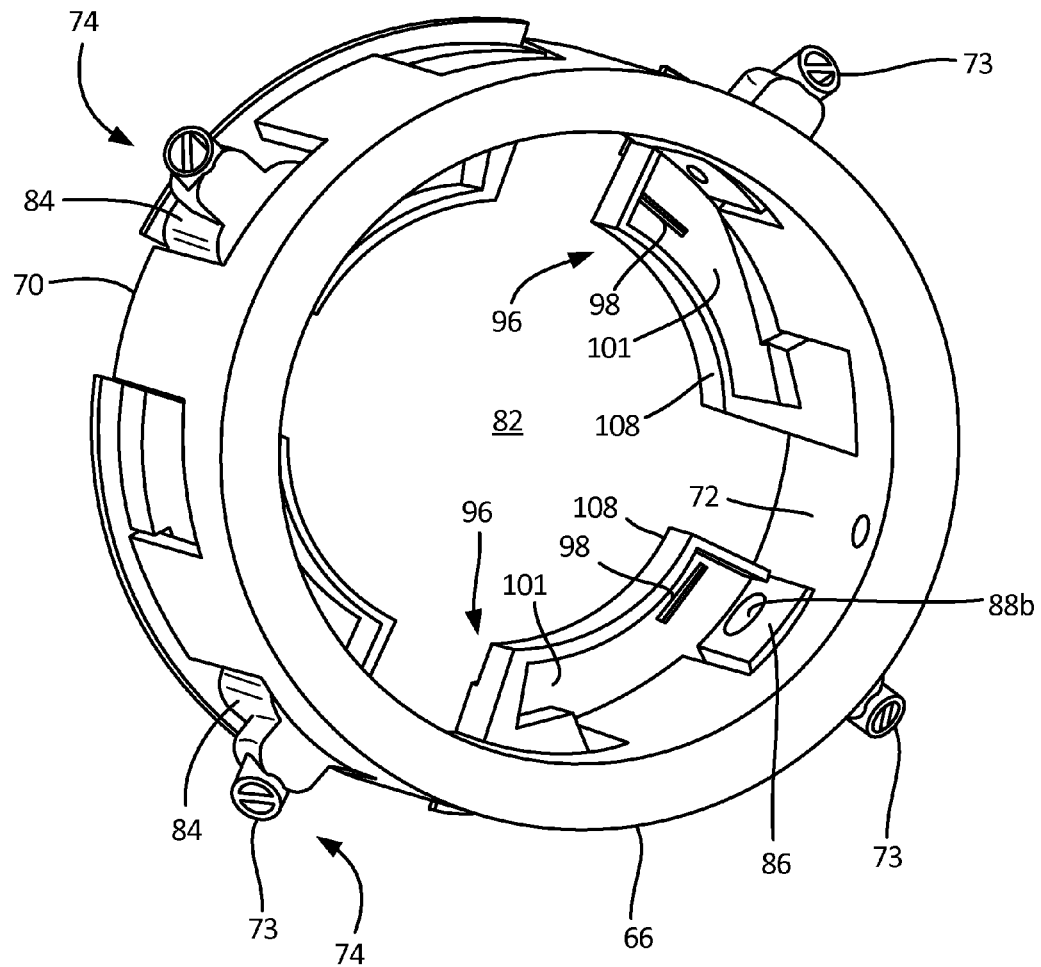
FIG. 12 is a perspective view of the ocular alignment device, according to certain embodiments.

According to further embodiments, best shown in FIGS. 6-10, disclosed is an alignment device 63 for aligning the eye 2 of a subject with an ocular imaging device (not shown). In these implementations the alignment device 63 comprises a housing 64 with a first end 66, a second end 68, an outer surface 70, and an inner surface 72 (as best shown in FIG. 7). The housing 64 first end 66 is configured to interface with an ocular imaging device (such as, for example, a device similar to the device 6 embodiments shown in FIGS. 1A-2B and 5) while the second end 68 is proximal to the eye 2 of the subject. According to certain implementations as best shown in FIGS. 7 and 11, the housing 64 is a substantially tubular shape defining a luminal space 82 defined by its inner surface 72 through which the optical path 80 (as shown in FIG. 6) between the optical imaging device and the eye 2 of the subject can pass. As best shown in FIGS. 7 and 12, a plurality of guide light assemblies 74 is arranged on the housing 64.

Figure 8A:
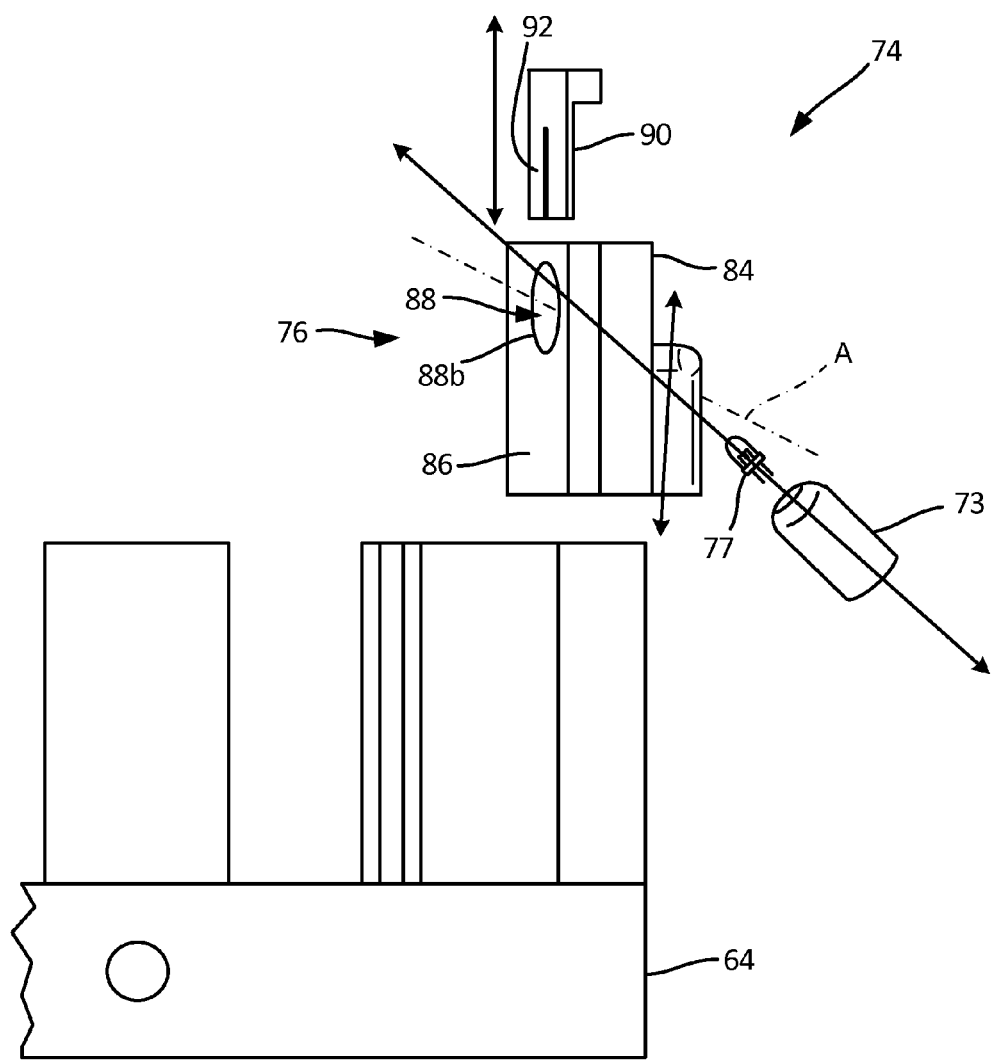
FIG. 8A is an exploded view of the guide light assembly, according to certain embodiments.
Figure 8B:
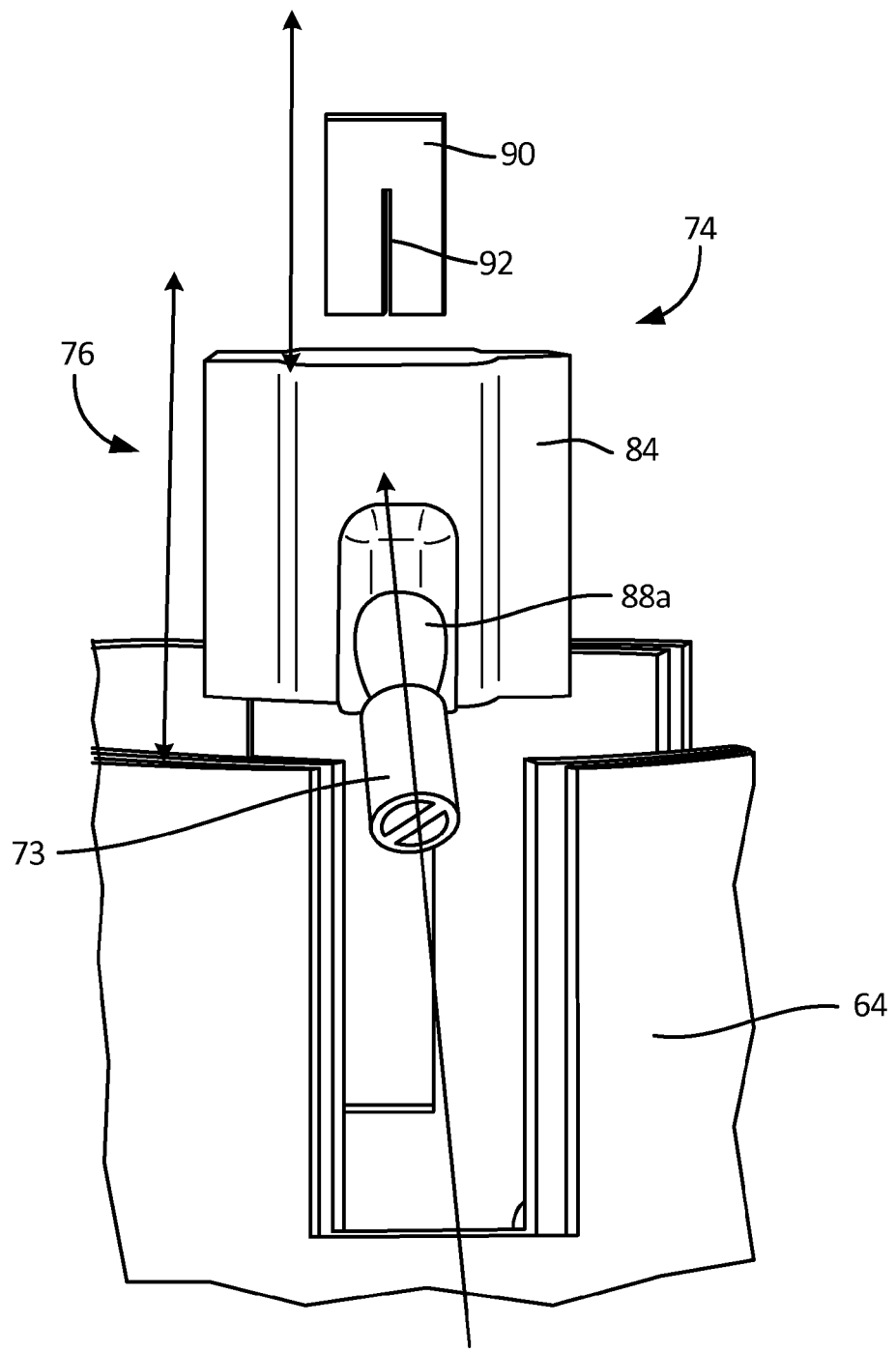
FIG. 8B is an exploded view of the guide light assembly, according to certain embodiments.

As best shown in FIGS. 7-8B, the guide light assemblies 74 comprise a body 76 having a first side 84 extending from the housing outer surface 70 and a second side 86 facing the luminal space 82. In certain implementations, also best shown in FIGS. 7-8B, the guide light assemblies 74 are slidably mounted into the housing 64 such that the user can adjust the position of the guide light assembly 74 along a longitudinal axis 71.

As best shown in FIGS. 8A and 8B, the guide light assembly body 76 defines a channel 88 extending from the guide light assembly body first side 84 to the second side 86 as best shown via the longitudinal axis depicted schematically via line A in FIG. 8A. The channel forms a first opening 88a on guide light assembly body first side 84 and a second opening 88b guide light assembly body second side 86. Disposed within the channel 88 is a guide light bezel 73 and a guide light 77 disposed within the guide light bezel 73 (best shown in FIG. 8A). As best shown in FIGS. 7 and 10-13, the guide light bezel 73 is disposed partially within the channel 88 such that a portion of the bezel 73 extends out of the channel 88 on the first side 84. In certain implementations, the guide light assembly may further comprise a power supply, housed within the body (not shown).

Continuing with FIGS. 8A and 8B, the guide light assembly 74 further comprises a baffle 90 positioned in the channel 88 at or near the second channel opening 88b on the second side 86 (disposed between the guide light 77 and the second channel opening 88b). As shown, the baffle 90 is positioned such that it is transverse to the longitudinal axis of the channel 88. The baffle 90 has a slit 92 defined in the baffle 90 that is positioned longitudinally along the length of the baffle 90. In use, the baffle 90 occludes rays emitted by the guide light 77, while the slit 92 permits passage of rays traveling along the alignment path 99 (best shown in FIG. 9A).

According to certain embodiments, the device further comprises a plurality of secondary baffle assemblies. 96 (best shown in FIGS. 7 and 10-13). According to certain embodiments, the plurality of secondary baffle assemblies 96 is arranged on the second end 68 of the housing 64 such that the baffle assemblies 96 extend inward toward the center of the luminal space 82, as best shown in FIG. 12. In certain implementations, as best shown in FIG. 7, the secondary baffle assemblies 96 are slidably mounted into the housing 64 such that the user can adjust the position of the secondary baffle assembly 96 along a longitudinal axis 71. As best shown in FIGS. 9 and 12, each of the secondary baffle assemblies 96 further comprise a baffle plate 101 and a baffle wall 108 extending into the luminal space 82, as mentioned above. The baffle plate 101 further comprises a slit 98.

Figure 9A:
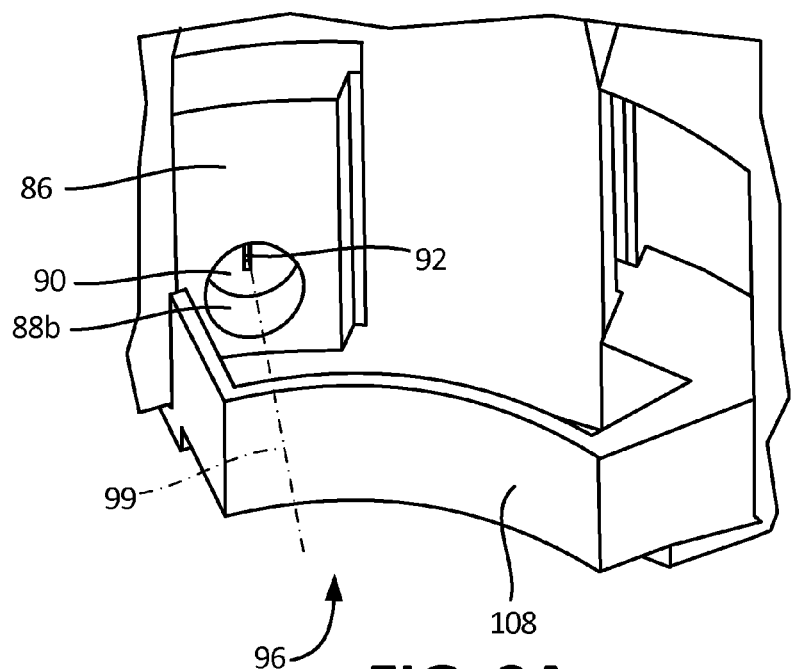
FIG. 9A shows a view a guide light assembly from the perspective of the luminal space, according to certain embodiments.
Figure 9B:
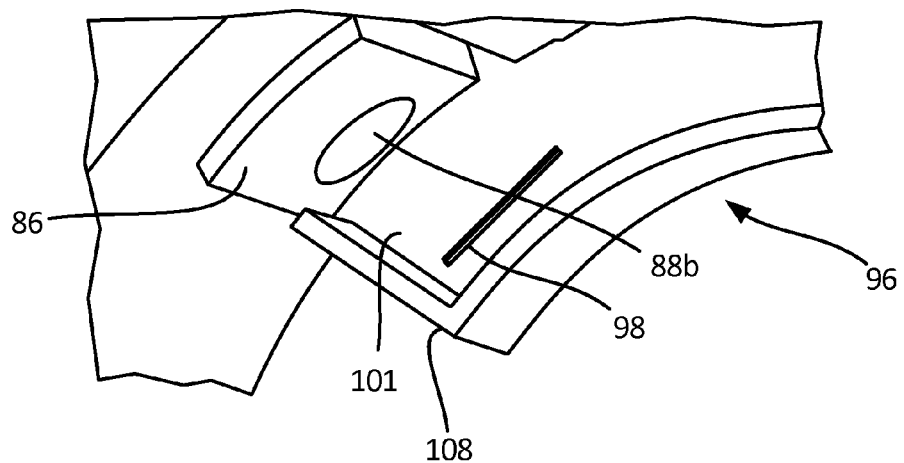
FIG. 9B shows a view a guide light assembly and a secondary baffle assembly from the perspective of the luminal space, according to certain embodiments.
Figure 9C:
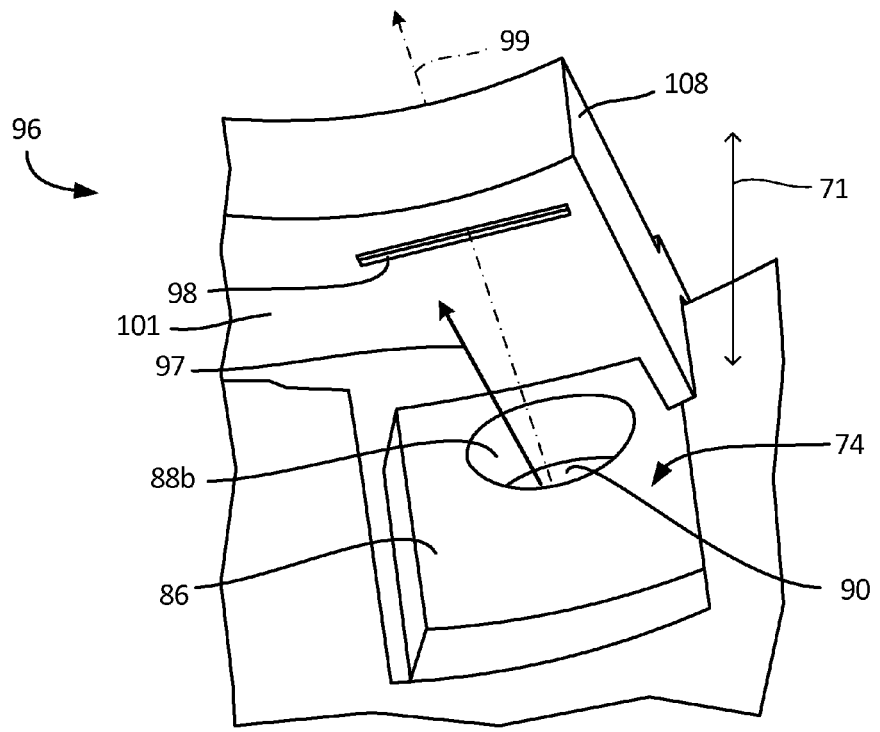
FIG. 9C shows a view a guide light assembly and a secondary baffle assembly from the perspective of the luminal space, according to certain embodiments.

As best shown in FIG. 9C, light 97 emitted from the slit (not shown) in the baffle 90 is further masked by the secondary baffle assembly 96, with the baffle plate 101 and the baffle wall 108 blocking light 97 not along the alignment path. The slit 98 mentioned above is configured to allow passage of guide light rays 99 along the path of alignment. As will be appreciated by a person having skill in the art, adjustment of the guide light assembly or the secondary baffle assembly 96 along the longitudinal axis 71 permits the adjustment of the angle at which the guide light rays 99 are emitted and masked. Such adjustment makes it possible to modify the alignment points with respect to the eye of the subject 2.

Figure 9D:
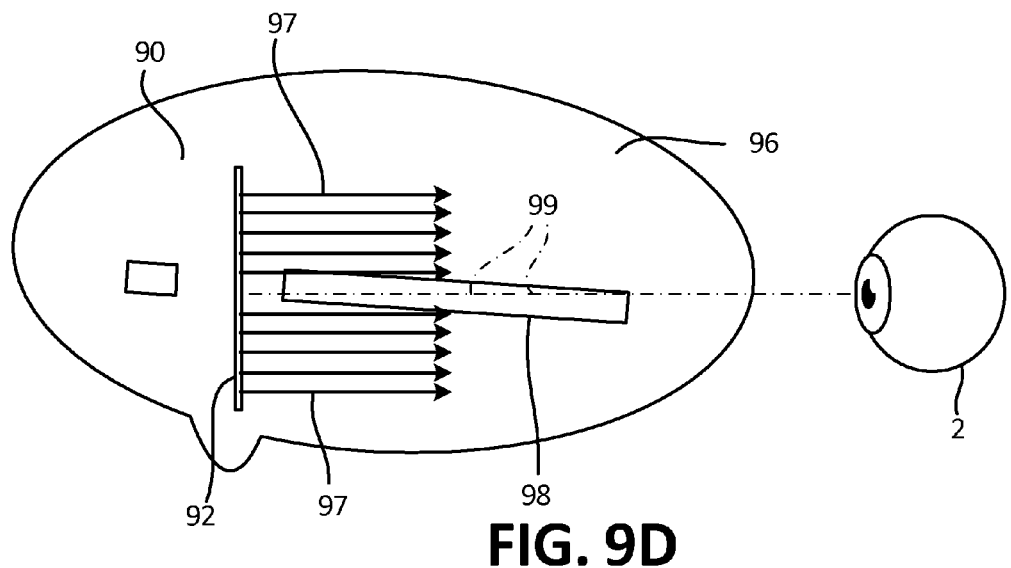
FIG. 9D shows a schematic diagram guide light masking by a guide light baffle and secondary baffle, according to certain implementations.
Figure 10:
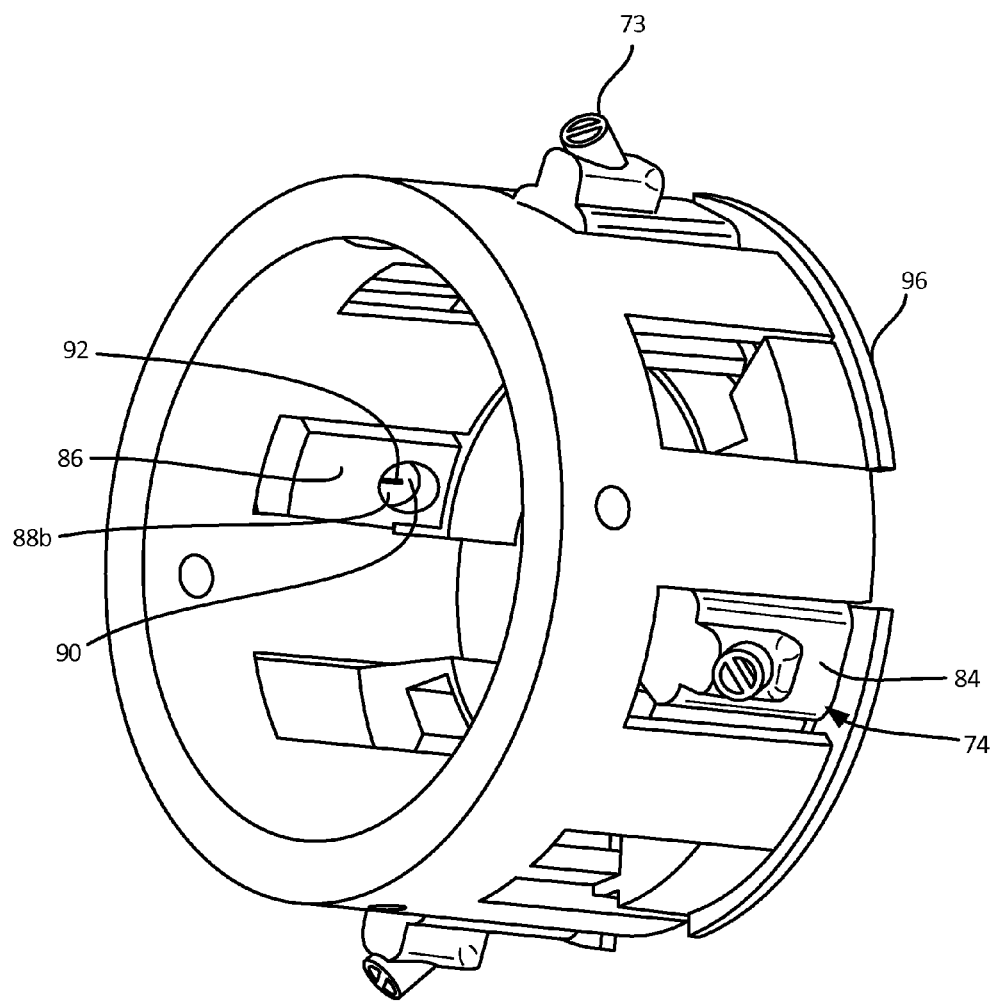
FIG. 10 is a perspective view of the ocular alignment device, according to certain embodiments.

According to certain embodiments, the baffle slit 92 and the secondary baffle assembly 96 slit 98 have a generally perpendicular orientation with respect to one another. FIG. 9D shows a schematic representation of the effect of slit orientation on light masking. As shown in that figure, rays 97 are emitted along the length of the baffle slit 92. The secondary baffle assembly 96 masks all rays 97 except for ray at the proper alignment path 99 which passes through the secondary baffle assembly slit 98 and is perceptible to the subject's eye 2, indicating proper alignment.

The disclosed devices and systems are capable of imaging multiple ocular regions. In certain embodiments, proper alignment is achieved when the subject's eye is aligned for imaging of the retina. In further embodiments, proper alignment is achieved when the subject's eye is aligned for imaging the cornea. In still further embodiment, proper alignment is achieved when the subject's eye is aligned for imaging the iris. In yet further embodiments, proper alignment is achieved when the subject's eye is aligned for imaging the lens. In further embodiments, proper alignment is achieved when the subject's eye is aligned for imaging the optic nerve head.

As will be appreciated by a person having skill in the art, the disclosed systems and devices can be used with numerous optical imaging systems. In certain embodiments, the optical imaging device is a fundus camera. In further embodiments, the camera is an optical coherence tomography (OCT) retinal camera. In still further embodiments, the optical imaging device is an autorefractor. In yet further embodiments, the optical imaging device is a corneal camera. As will be appreciated by one skilled in the art, other camera types are possible.

According to certain embodiments, the system further comprises one or more indicator signals. In these embodiments, each indicator signal serves to provide additional guidance to the subject regarding the required direction of eye movement to achieve alignment. Example indicator signals include, but are not limited to, arrows, colors, or flashing lights. In certain implementations, sounds and/or other non-visual feedback cues are also possible. According to certain embodiments, the indicator signals are masked by one or more baffles such that they are only visible when the eye is out of alignment. For example, a rightward pointing arrow indicator signal is baffled such that it is only visible to the subject when the subject eye is directed to the left of proper alignment.

Figure 14A:
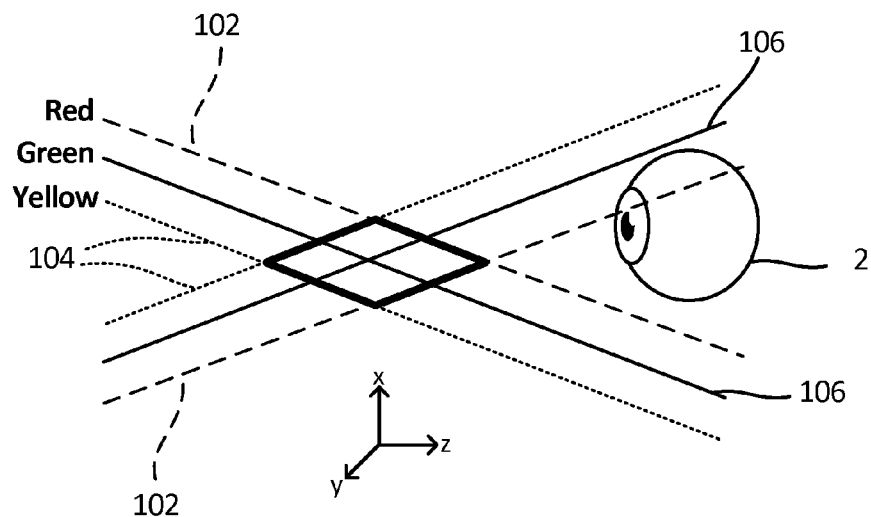
FIGS. 14A and 14B are schematic diagrams of indicator signals according to certain embodiments.
Figure 14B:
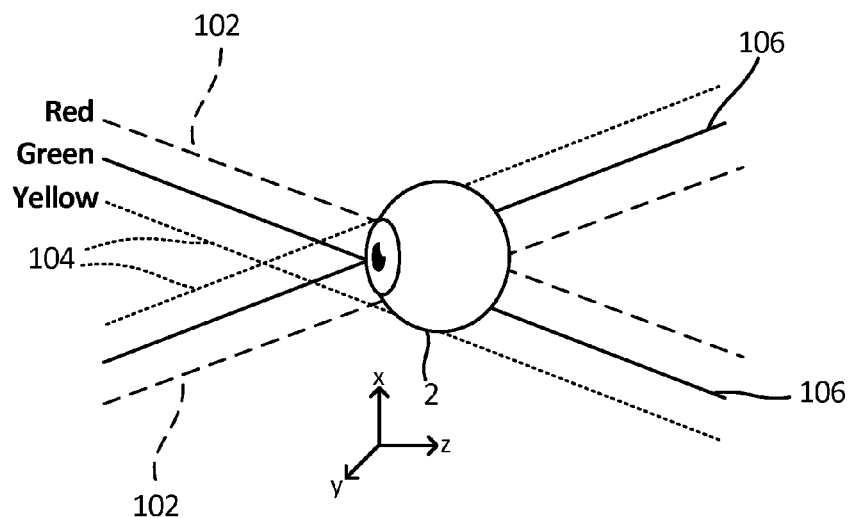

According to certain embodiments, indicator signals are comprised of colored ring lights of differing colors (not shown). The one or more guide lights is a color different from the colors of the one or more indicator signal. FIG. 14A shows an eye of a subject 2 out of alignment where the subject is able to view a red indicator signal light 102 but unable to see the green guide light 106. Similarly, if the subject is able to view the yellow indicator signal 104, its eye 2 is not in proper alignment. FIG. 14B shows an eye of a subject in proper alignment where the subject is able to see the green guide light 106 but unable to see the yellow 104 or red indicator signals 106. According to certain embodiments, (not shown) the indicator signal the subject is able to view conveys information to the subject about the direction the eye needs to adjust in order to achieve proper alignment.

In certain aspects, disclosed is a device for aligning a subject's eye with an optical axis of an ocular imaging device comprising a housing, the housing comprising a first end, a second end, an outer surface, and an inner surface, wherein the inner surface defines a luminal space and wherein the luminal space is configured to allow for passage of the optical axis therethrough; a plurality of guide light assemblies disposed within the housing, each guide light assembly comprising a body, the body comprising a first side and a second side opposite the first side, wherein the second side faces the luminal space a channel defined in the body, wherein the channel extends from the body first side to the body second side, wherein the channel forms an opening in the body second side; a guide light disposed within the channel, wherein the guide light is configured to emit rays out of the opening; and a baffle disposed transversely in the channel between the guide light and the opening and configured to mask rays from the guide light, wherein the baffle further comprises a slit configured to allow passage of rays along a path of ocular alignment; and a plurality of secondary baffle assemblies disposed on the housing second end, wherein each of the plurality of second baffle assemblies is configured to mask rays emitted from one of the plurality of guide light assemblies, wherein each of secondary baffle assemblies further comprises a slit configured to allow passage of rays along a second path of ocular alignment, wherein the light from each of the plurality of guide light assemblies is visible to the subject when the subject's eye is in alignment with respect to the optical axis and not visible when the optical axis of the subject's eye is out of alignment with respect to the optical axis.

According to further aspects the plurality of guide light assemblies are slideably mounted to the housing. In yet further aspects, the plurality of secondary baffle assemblies are slidably mounted to the housing. In yet further aspects, the secondary baffle assemblies each further comprise a baffle plate, wherein the slit is positioned on the baffle plate, and a baffle wall, the baffle wall extends into the luminal space of the housing toward the housing first end. In even further aspects, at least one of the plurality of secondary baffle assemblies is comprised of anti-reflective material.

In certain implementations, the disclosed device further comprises a co-axial light, visible to the subject when the subject's is in coarse alignment. In certain aspects, the disclosed device further comprises a first set of the plurality of guide lights wherein the first set of guide lights is visible to the subject when the optical axis of the subject's eye is in alignment along a x-axis with respect to the optical axis of the ocular device; and a second set of guide lights, visible to the subject when the optical axis of the subject's eye is in alignment along a y-axis with respect to the optical axis of the ocular device, wherein when the first set of guide lights and second set of guide lights are simultaneously visible to the subject, the subject's eye is in alignment with the z-axis.

In certain aspects, disclosed is an ocular alignment system for aligning the optical axis of a subject's eye with an optical axis of an ocular imaging device comprising a plurality of guide lights; and one or more baffle configured to mask the one or more guide light from view of the subject such that the one or more guide light is only visible to the subject when the optical axis of the subject's eye is aligned with the optical axis of an ocular imaging system.

In further aspects, at least one of the plurality of guide light is a ring light. In still further aspects, a set of the plurality of the plurality of guide lights is perceptible to the subject as varying spatial patterns indicating the direction of eye movement required for alignment. In yet further aspects, each of the plurality of guide lights is comprised of a distinct light source. In even further aspects, the disclosed system further comprises one or more sets of guide lights wherein one or more guide lights or regions of guide lights are turned on or off in different patterns for different optical fixation points.

In further aspects one or more baffle is a cone. In still further aspects, the one or more baffle further comprises one or more slits, configured to allow passage of rays along the alignment path. In even further aspects, the one or more baffles further comprises an air cavity or light absorption materials in combination or separately to minimize guide light reflection. In further aspects, the plurality of baffles or guide lights are adjustable to control a z-axes focal point to the subject's eye.

According to certain aspects, the disclosed system further comprising a first set of the plurality of guide lights wherein the first set of guide lights is visible to the subject when the subject's eye is in alignment along a x-axis with respect to the optical axis; and a second set of guide lights, visible to the subject when the subject's eye is in alignment along a y-axis with respect to the optical axis, wherein when the first set of guide lights and second set of guide lights are simultaneously visible to the subject, the subject's eye is in alignment with the z-axis. In still further aspects, a set of the plurality of guide light is only visible when the eye is aligned along the x, y and z axes with respect to the optical path of the ocular imaging device. In yet further aspects, the one or more guide light sources is positioned in the x-y plane at varying z-distance to optimize guide light path(s) to the subject. According to certain aspects, the one or more guide light is only visible when the eye is aligned along the $\theta$, $\eta$, and $\zeta$ axes with respect to the optical path of the ocular imaging device.

According to certain implementations, the disclosed system further comprises one or more indicator signals, wherein the one or more indicator signals indicates to the subject a direction of eye movement to achieve alignment. In certain aspects, the disclosed system further comprises one or more baffles to mask the one or more indicator signals from view of the subject such that the one or more indicator signal is only visible to the subject when the optical axis of the eye of the subject is out of alignment with the optical axis or a target operational distance of the ocular imaging system. In certain aspects, one or more indicator signals are arrows. In further aspects, the one or more indicator signals are colored lights.

According to certain aspects, the disclosed ocular alignment system is integrated within optical imaging device. In further aspects, the ocular alignment system is external to the optical imaging device.

According to certain implementations, the disclosed system further comprises a coaxial light, visible to the subject when coarse alignment is achieved.

In certain aspects, disclosed is a method of aligning a subject's eye with an optical axis of an ocular imaging device comprising providing a first set of guide lights along the optical path between the subject's eye and the ocular imaging device and providing one or more baffle, configured to mask the first set of guide lights from view of the subject such that first set of guide lights is only visible to the subject when the optical axis of the subject's eye is aligned with the optical axis of an ocular imaging system.

In certain aspects, the first set of guide lights is visible to the subject when the optical axis of the subject's eye is in alignment along a x-axis with respect to the optical axis of the ocular imaging device, and the method further comprises providing a second set of guide lights, visible to the subject when optical axis of the subject's eye is in alignment along a y-axis with respect to the optical axis of the ocular imaging device; and wherein when the first set of guide lights and second set of guide lights are simultaneously visible to the subject, the subject's eye is in alignment with the z-axis.

In certain aspects, the disclosed method further comprises providing a set of indicator lights visible to the subject when the subject's eye is out of alignment. In yet further aspects the indicator signals are comprised of no-visual signals, including but not limited to auditory and tactile indicator signals. In further aspects, the disclosed method further comprises providing a sequence of guide lights, wherein each guide light in the sequence brings the subject's eye closer to alignment along the z-axis with respect to the optical axis of the ocular imaging system.

Although the present invention has been described with reference to preferred embodiments, persons skilled in the art will recognize that changes may be made in form and detail without departing from the spirit and scope of the invention.

What is claimed is:

1. A device for aligning a subject's eye with an optical axis of an ocular imaging device comprising:
   a. a housing comprising a first end, a second end, an outer surface, and an inner surface, wherein the inner surface defines a luminal space and wherein the luminal space is configured to allow for passage of the optical axis therethrough;
   b. a plurality of guide light assemblies disposed within the housing, each guide light assembly comprising:
      i. a body comprising a first side and a second side opposite the first side, wherein the second side faces the luminal space;
      ii. a channel defined in the body, wherein the channel extends from the body first side to the body second side, wherein the channel forms an opening in the body second side;
      iii. a guide light disposed within the channel, wherein the guide light is configured to emit light out of the opening; and
      iv. a baffle disposed transversely in the channel between the guide light and the opening and configured to mask light from the guide light, wherein the baffle further comprises a slit configured to allow passage of light along a path of ocular alignment; and
   c. a plurality of secondary baffle assemblies disposed on the housing second end, wherein each of the plurality of second baffle assemblies is configured to mask light emitted from one of the plurality of guide light assemblies, wherein each of secondary baffle assemblies further comprises a slit configured to allow passage of light along a second path of ocular alignment,
   wherein the light from each of the plurality of guide light assemblies is visible to the subject when the subject's eye is in alignment with respect to the optical axis of the ocular imaging device and not visible when the subject's eye is out of alignment with respect to the optical axis of the ocular imaging device.

2. The device of claim 1, wherein the plurality of guide light assemblies are slideably mounted to the housing.

3. The device of claim 1, wherein the plurality of secondary baffle assemblies are slidably mounted to the housing.

4. The device of claim 1, wherein the secondary baffle assemblies each further comprise a baffle plate, wherein the slit is positioned on the baffle plate, and a baffle wall.

5. The device of claim 4, wherein the baffle wall extends into the luminal space of the housing toward the housing first end.

6. The device of claim 1, wherein the secondary baffle assembly are comprised of anti-reflective material.

7. The device of claim 1, further comprising a co-axial light, visible to the subject when the subject's is in course alignment.

8. The device of claim 1, further comprising a first set of the plurality of guide lights wherein the first set of guide lights is visible to the subject when the subject's eye optical axis is in alignment along the x-axis with respect to the optical axis of the imaging system; and a second set of guide lights, visible to the subject when the subject's eye optical axis is in alignment along a y-axis with respect to the optical axis of the imaging system, wherein when the first set of guide lights and second set of guide lights are simultaneously visible to the subject, the subject's eye is in alignment with the z-axis of the imaging system.

9. An ocular alignment system for aligning the optical axis of a subject's eye with an optical axis of an ocular imaging device comprising:
   a. a first set of a plurality of guide lights visible to the subject when the optical axis of the subject's eye is in alignment along the x-axis with respect to the optical axis of the ocular imaging system; and a second set of guide lights, visible to the subject when the subject's eye is in alignment along a y-axis with respect to the optical axis of an ocular imaging system, wherein when the first set of guide lights and second set of guide lights are simultaneously visible to the subject, the subject's eye is in alignment with the z-axis; and
   b. one or more baffle configured to mask the one or more guide light from view of the subject such that the one or more guide light is only visible to the subject when the optical axis of the subject's eye is aligned with the optical axis of an ocular imaging system.

10. The system of claim 9 wherein the one or more baffle further comprises one or more slits, configured to allow passage of light along the alignment path.

11. The system of claim 9 wherein the plurality of baffles or guide lights are adjustable to control a z-axes focal point to the subject's eye.

12. The system of claim 9 wherein a set of the plurality of guide light is only visible when the eye is aligned along the x, y and z axes with respect to the optical path of the ocular imaging device.

13. The system of claim 9, where the one or more guide light sources is positioned in the x-y plane at varying z-distance to optimize guide light path(s) to the subject.

14. The system of claim 13 wherein the one or more guide light is only visible when the eye is aligned along the $\theta$, $\eta$, and $\zeta$ axes with respect to the optical path of the ocular imaging device.

15. The system of claim 9, further comprising one or more indicator signals, wherein the one or more indicator signals indicates to the subject a direction of eye movement to achieve alignment.

16. The system of claim 15, further comprising one or more baffle to mask the one or more indicator signal from view of the subject such that the one or more indicator signal is only visible to the subject when the eye of the subject is out of alignment with the optical axis or a target operational distance of the ocular imaging system.

17. The system of claim 9 further comprising a coaxial light, visible to the subject when coarse alignment is achieved.

18. A method of aligning a subject's eye with an optical axis of an ocular imaging device comprising:
   a. providing a first set of a plurality of guide lights visible to the subject when the optical axis of the subject's eye is in alignment along the x-axis with respect to the optical axis of the ocular imaging system; and a second set of guide lights, visible to the subject when the subject's eye is in alignment along a y-axis with respect to the optical axis of an ocular imaging system, wherein when the first set of guide lights and second set of guide lights are simultaneously visible to the subject, the subject's eye is in alignment with the z-axis; and
   b. providing one or more baffle, configured to mask the first set of guide lights from view of the subject such that first set of guide lights is only visible to the subject when the eye of the subject is aligned with the optical axis of an ocular imaging system.

19. The method of claim 18, further comprising providing one or more indicator signals, wherein the one or more indicator signals indicates to the subject a direction of eye movement to achieve alignment.

* * * * *